US00PP08111P

United States Patent [19]

Dehan

[11] Patent Number: Plant 8,111

[45] Date of Patent: Jan. 19, 1993

[54] IMPATIENS PLANT NAMED RONDO

[75] Inventor: Klara Dehan, Holon, Israel

[73] Assignee: Danziger - "Dan" Flower Farm, Post Beit Dagan, Israel

[21] Appl. No.: 730,610

[22] Filed: Jul. 16, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new Impatiens plant named Rondo, characterized by its dark red medium size flower color, compact growth, medium size plant, floriferous habit, and by its purple stems.

1 Drawing Sheet

The present invention relates to a new and distinctive cultivar of Impatiens plant, botanically knows as Impatiens and known by the cultivar name Rondo, developed by me through controlled breeding by crossing the cultivar identified by its breeding number 0-5-G as the seed parent with the cultivar identified by the number 68-5-A as the pollen parent.

Asexual reproduction by terminal or stem cuttings taken at Mishmar Hashiva, Israel has shown that the unique features of this new Impatiens are stabilized and are reproduced true to type in successive propagations.

The following characteristics distinguish the new Impatiens from both its parent varieties and other cultivated impatiens of this type known and used in the floriculture industry:

1. Compact growth habit.
2. Medium size plant.
3. Unique dark red flower color.
4. Medium size flower.
5. Floriferous habit.
6. Flower carried on purple stems.
7. The compact and vigorous growth habit of Rondo is unique for bright red flower cultivars of this type.

The accompanying color photographs illustrate the overall appearance and flower detail of this cultivar, showing the colors as true as it is reasonably possible to obtain in a colored reproduction of this type.

The top photo is a top perspective view of a portion of a plant.

The bottom photo is an enlarged showing of a single flower.

The following is a detailed description of my new impatiens cultivar based on plants produced under commercial practice in Mishmar Hashiva, Israel. The description is based on observations and measurements made in the winter and the early spring.

Color references are made to The Royal Horticultural Society Colour Chart except where general terms of ordinary dictionary significance are used.

Parentage: Cross of 0.5.G × 68-5-A.

Propagation:

A. *Type cutting.*—Leaf cuttings with axillary buds but not flower buds.

B. *Time to initiate roots.*—8–10 days both at 25°–30° C. summer and 20°–22° C. winter.

C. *Rooting habit.*—Good root initiation.

Plant description:

A. *Form.*—Compact, medium size plant, symmetrically mounted.

B. *Habit of growth.*—Excellent branching and vigorous.

C. *Foliage description.*—Small to medium size leaves, dark green in color. (1) Size: Approximately 7.5 cm in length and 3.5 cm in width. (2) Shape: Oval to elliptical. (3) Margin: Serrated. (4) Color: Young foliage top side darker than 137A; under side 146 B-C. Mature foliage top side darker than 137A; under side 146 B-C. (5) Venation: Light green.

Flowering description:

A. *Flowering habits.*—Very floriferous, with bud to fully open flower requiring approximately five days.

B. *Natural flowering season.*—Spring in moderate climates, but in Israel also in the winter.

C. *Flower bud description.*—Normal.

D. *Flowers borne.*—Every branch has 5–6 buds in different stages. There are up to 3 opened flowers at the same time on each branch. Flower stems are purple in color.

E. *Quantity of flowers.*—Total inflorescence is about 30–35 opened flowers at the same time, creating an extensive canopy of color. Flowering is continuous at temperatures above approximately 10° C. and with minimum levels of light.

F. *Petals.*—(1) Shape: Two pairs of heart shaped petals, and one non-heart shaped. (2) Color: Top side when opening 46B, with little or no fading of the bright and intense red color; under side 51A. (3) Number of petals: Five. (4) Size of flowers: Approximately 5.5 cm in total diameter.

G. *Reproductive organs.*—(1) Stamens: One in number. (a) Anthers: White and purple in color. (b) Pollen color: White. (2) Pistils: (a) Stigma: Cone shaped, green in color. (b) Style: Green in color. (c) Ovaries: One in number, size 1.5 mm, color, light green.

I claim:

1. A new and distinct cultivar of Impatiens plant named Rondo, as illustrated and described.

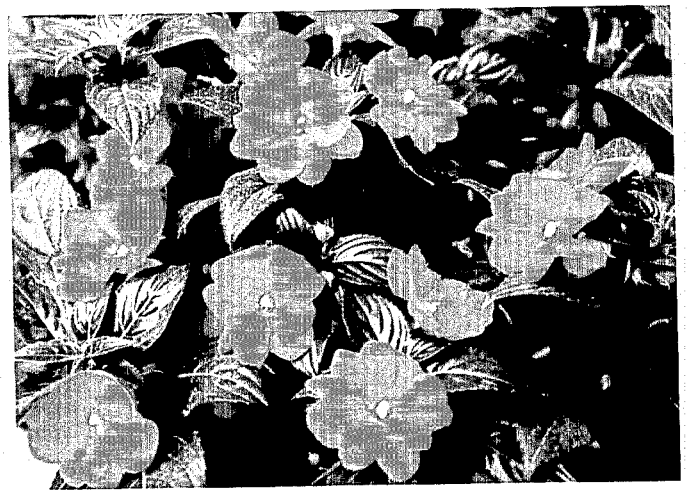
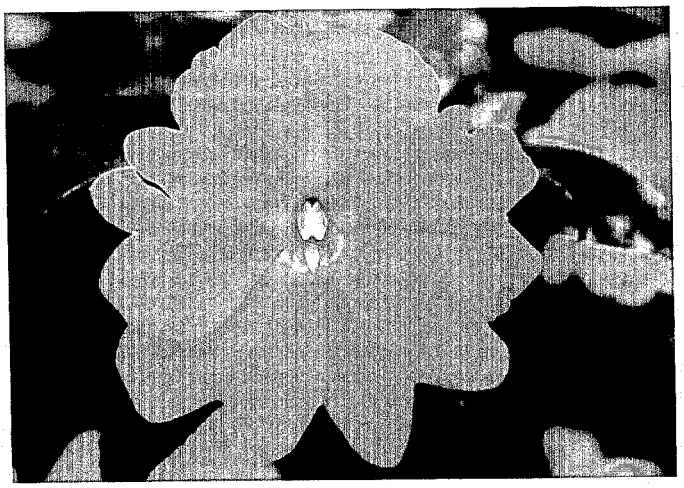

* * * * *